(12) United States Patent
Flechsig et al.

(10) Patent No.: US 8,216,446 B1
(45) Date of Patent: Jul. 10, 2012

(54) METHOD FOR LABELLING AND ANALYSING NUCLEIC ACIDS

(75) Inventors: Gerd-Uwe Flechsig, Teterow (DE); Thomas Reske, Rostock (DE)

(73) Assignee: Universität Rostock, Rostock (DE)

( * ) Notice: Subject to any disclaimer, the term of this patent is extended or adjusted under 35 U.S.C. 154(b) by 518 days.

(21) Appl. No.: 11/990,666

(22) PCT Filed: Aug. 17, 2006

(86) PCT No.: PCT/EP2006/008131
§ 371 (c)(1),
(2), (4) Date: Feb. 19, 2008

(87) PCT Pub. No.: WO2007/020093
PCT Pub. Date: Feb. 22, 2007

(30) Foreign Application Priority Data

Aug. 19, 2005 (DE) .......................... 10 2005 039 726

(51) Int. Cl.
*C12Q 1/68* (2006.01)
*G01N 27/327* (2006.01)

(52) U.S. Cl. ...................... 205/777.5; 435/6; 204/403.14
(58) Field of Classification Search .................... 435/6; 204/403.01–403.15; 205/777.5, 775, 792
See application file for complete search history.

(56) References Cited

FOREIGN PATENT DOCUMENTS

| | | |
|---|---|---|
| DE | 101 06 654 | 2/2001 |
| EP | 0 435 470 A1 | 7/1991 |
| WO | WO 02/16647 | 2/2002 |
| WO | WO 2005/005952 | 1/2005 |

OTHER PUBLICATIONS

Flechsig Gu, Peter J, Hartwich G, Wang J, Gründler P. "DNA hybridization detection at heated electrodes." *Langmuir* 21(17):7848-7853 (2005).
Flechsig Gu, Reske T. "Electrochemical detection of DNA hybridization by means of osmium tetroxide complexes and protective oligonucleotides." *Anal. Chem.* 79(5): 2125-30 (2007).
Fojta M, Havran L, Billova S, Kostecka P, Masarik M, and Kizek R. "Two-Surface Strategy in Electrochemical DNA Hybridization Assays: Detection of Osmium-Labeled Target DNA at Carbon Electrodes." *Electroanalysis* 15(5-6):431-40 (2003).
Fojta, M., Havran, L., Kizek, R., Billova, S. Palecek, E. "Multiply osmium-labeled reporter probes for electrochemical DNA hybridization assays: detection of trinucleotide repeats." *Biosensors and Bioelectronics* 20:985-994 (2004).
Fojta M, Havran L, Vojtiskova M, Palecek E. "Electrochemical detection of DNA triplet repeat expansion." *J. Am. Chem. Soc.* 126(21):6532-33 (2004).
Herne TM and Tarlov MJ. "Characterization of DNA Probes Immobilized on Gold Surfaces." *J. Am. Chem. Soc.* 119(38): 8916-20 (1997).
Kostecka P, Havran L, Pivonkova H, Fojta M. "Voltammetry of osmium-modified DNA at a mercury film electrode: application in detecting DNA hybridization." *Bioelectrochemistry* 63(1-2): 245-48 (2004).

(Continued)

*Primary Examiner* — Kaj K Olsen
*Assistant Examiner* — Kourtney R Salzman
(74) *Attorney, Agent, or Firm* — Ballard Spahr LLP

(57) ABSTRACT

The invention relates to a method of labelling and analysing nucleic acids. More specifically, the invention relates to a method of analysing nucleic acids, which comprises contacting the nucleic acids to be detected, which are in the form of single-stranded nucleic acid strands partially (i.e. over a part of the total length of the nucleic acid strands) hybridized with protective strands, with substances which specifically react with nucleobases of the single-stranded sections of the nucleic acid strands, and which are capable of subsequently participating in a reversible redox reaction in electroanalytical processes known to the skilled worker.

15 Claims, 6 Drawing Sheets

OTHER PUBLICATIONS

Lucarelli F, Marrazza G, Turner AP, Mascini M. "Carbon and gold electrodes as electrochemical transducers for DNA hybridisation sensors." *Biosens. Bioelectron*, 19(6): 515-30 (2004).

Palecek E, Fojta M. "Detecting DNA hybridization and damage." *Anal. Chem.* 73(3): 74-83A (2001).

Steel AB, Herne TM, Tarlov MJ. "Electrochemical quantitation of DNA immobilized on gold." *Anal. Chem.* 70(22): 4670-77 (1998).

Umek RM, Lin SW, Vielmetter J, Terbrueggen RH, Irvine B, Yu CJ, Kayyem JF, Yowanto H, Blackburn GF, Farkas DH, Chen YP. "Electronic detection of nucleic acids: a versatile platform for molecular diagnostics." *J. Mol. Diagn.* 3(2): 74-84 (2001).

Zerihun T and Gründler P. "Electrically heated cylindrical microelectrodes: Determination of lead on pt by cyclic voltammetry and cathodic stripping analysis." *J. Electroanal. Chem.* 415(1-2): 85-88 (1996).

Zerihun T and Gründler P. "Electrically heated cylindrical microelectrodes. The reduction of dissolved oxygen on Pt." *J. Electroanal. Chem.* 404(2): 243-48 (1996).

International Search Report mailed on Feb. 22, 2007 (PCT EP2006/008131).

International Preliminary Report on Patentability mailed on Mar. 4, 2008 (PCT EP2006/008131).

Written Opinion mailed on Mar. 4, 2008 (PCT EP2006/008131).

ized signals. Accordingly, the detection ranges of suitable compounds are in a potential range which can be readily achieved on inexpensive electrodes such as gold, platinum, carbon etc. The potential range is between -1 V and +1 V.

METHOD FOR LABELLING AND ANALYSING NUCLEIC ACIDS

CROSS REFERENCE TO RELATED APPLICATIONS

The present application is a National Phase Application of International Application No. PCT/EP2006/008131, filed Aug. 17, 2006, which claims priority to German Patent Application No. 10 2005 039 726.3, filed Aug. 19, 2005, which applications are incorporated herein fully by this reference.

The invention relates to a method of labelling and analysing nucleic acids. More specifically, the invention relates to a method of analysing nucleic acids, which comprises contacting the nucleic acids to be detected, which are in the form of single-stranded nucleic acid strands partially (i.e. over a part of the total length of the nucleic acid strands) hybridized with protective strands, with substances which react specifically with nucleobases of the single-stranded sections of the nucleic acid strands, and which are capable of subsequently participating in a reversible redox reaction in electroanalytical processes known to the skilled worker.

PRIOR ART

In order to enable hybridization events of nucleic acids to be detected electrochemically, use is frequently made of redox-active molecules which are covalently attached either to the target strand or to a reporter strand, bind electrostatically to the phosphate groups of the nucleic acids, or insert themselves as intercalators into the double strand. The covalently attached "redox markers" are attached during production of the target strands or reporter strands.

Alternatively, it is possible to use osmium(VIII) oxide by way of complexes with 2,2'-bipyridine, [OsO4(bipy)]. These complex compounds react specifically with the pyrimidine bases thymine, uracil and, to a much lesser extent, cytosine, attacking the double bond in the pyrimidine ring. This reaction does not occur within an intact double strand. On the other hand, single strands whose pyrimidine bases have reacted with osmium complexes are no longer able to form double strands. These relationships have been studied by Palecek, Jelen and Foita since the early 1980s and were used in the form of numerous examples for detecting hybridization. Reference is made to the following publications which are hereby expressly incorporated by reference: M. Foita et al., J. Am. Chem. Soc. 126 (2004) 6532; P. Kostecka et al., Bioelectrochemistry 63 (2004) 245; M. Foita et al., Electroanalysis 15 (2003) 431.

DNA may be modified by means of osmium(VIII) complexes very easily by adding the osmium reagent to the analytical solution. Excess reagent is removed after modification by dialysis in commercially available simple dialysis vessels. For this purpose, hybridization of target and probe is optimally conducted on different surfaces.

Particularly suitable are "magnetic beads" whose surface carries immobilized probe strands and which can be separated from the analytical solution (and thus from non-complementary strands and analytical reagents) by means of a magnetic field. Any nucleic acid strands could be labelled according to this principle. Disadvantageously, however, different reaction areas must be used in order to perform both hybridization and electrochemical detection. The problem of osmium-modified nucleic acid single strands no longer being able to form double strands and, on the other hand, of intact double strands not reacting with [OsO4(bipy)] has not been solved satisfactorily thus far. It would be desirable to label PCR products or native nucleic acid samples with osmium compounds, without the ability to hybridize being lost. The large number of osmium units bound to the target strands would produce a very high sensitivity in the subsequent electrochemical analysis. Another disadvantage is the toxicity of osmium compounds, which would make it desirable to replace them with less toxic substances that react in a similar way with nucleic acids.

It is therefore the object of the invention to provide a method which enables any nucleic acid strands to be labelled rapidly and easily, and immediately thereafter allows electrochemical detection on a working electrode.

DESCRIPTION OF THE INVENTION

This object is achieved by a method which comprises contacting the nucleic acid to be detected, which is in the form of single-stranded nucleic acid strands partially (i.e. over a part of the total length of the nucleic acid strands) hybridized with protective strands, with substances which react specifically with nucleobases (pyrimidine rings) of the single-stranded sections of the nucleic acid strands, and which are capable of subsequently participating in a reversible redox reaction in electroanalytical processes known to the skilled worker.

Preference is given here to using compounds which belong to either of the following two classes of substances: 1. osmium tetroxide complexes, and 2. compounds comprising both a 1,3-diene structure and at least one electrochemically reversibly reacting group. These two classes of substances make possible both a selective reaction with the double bond of the pyrimidine ring and electroanalytically utilizable reversible redox reactions on working electrodes. Substance class 1 in particular includes [OsO$_4$(bipy)] and [OsO$_4$(py)$_2$]. Substance class 2 in particular includes 7,8-bis(methylene)-6,9-dihydronaphthoquinone

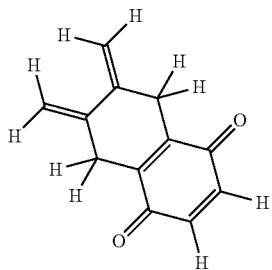

and heteroanalogous derivatives thereof.

Examples which may also be mentioned here further are organic compounds having both a 1,3-diene component and a quinone ring. The 1,3-diene component makes a Diels-Alder reaction with the double bond of the pyrimidine ring possible, while quinone (1,4-dihydroxobenzene) is reversibly electrochemically active.

According to a preferred embodiment of the invention, the redox markers used are osmium(VIII) compounds such as [OsO$_4$(bipy)] and [OsO$_4$(py)$_2$], for example. Preference is given according to the invention to the complex of osmium tetroxide with 2,2'-bipyridine, [OsO$_4$(bipy)]

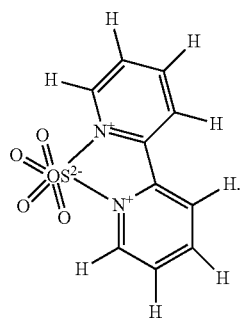

Figure 1:
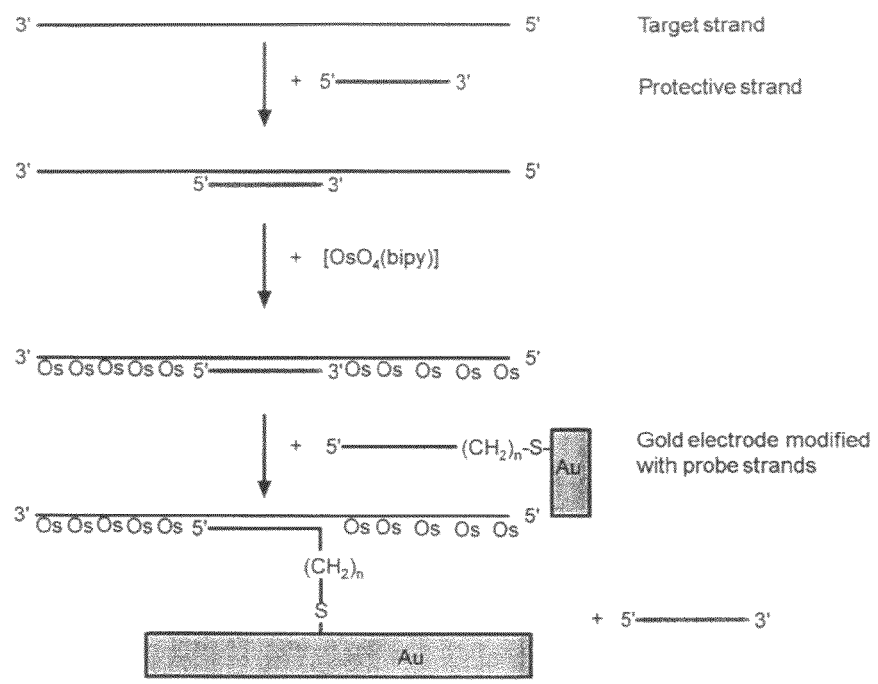
FIG. 1 schematically depicts the method according to the invention by way of a specific example.

FIG. 1 schematically depicts the method according to the invention by way of a specific example.

The invention in particular relates to a method of detecting nucleic acid strands by labelling with redox markers and electrochemical detection of hybridization events, wherein
a) single-stranded nucleic acid strands (target strands) are hybridized with one or more nucleic acid strands (protective strands A) which are shorter than the target strands in order to form partial double-stranded sections,
b) the remaining single-stranded sections of the target strands are labelled by reaction with redox markers which comprise either osmium tetroxide or 1,3-diene structures, so that they selectively react with the double bond of the pyrimidine rings of the nucleic acid strands and, owing to the resulting osmium(VI) compounds or to additional redox-active structures or hetero analogues thereof (quinones, naphtha quinones, diaminonaphthalenes, diaminobenzenes, anthraquinones, phenothiazones, dihydroxybenzenes, phenylenediamines, tetrathiazanes, tetrathiafulvalenes or their corresponding redox partners) present in the redox marker molecule, make possible a (reversible) electroanalytically utilizable redox reaction on working electrodes (in particular working electrodes of metal, carbon, polymers, semiconductors, indium tin oxide) on which the probe strands have been immobilized,
c) the nucleic acid strands labelled in this way are hybridized on the surface of an electrode with probe strands immobilized there, with the protective strands A being displaced, and
d) the nucleic acid strands hybridized to the probe strands are then detected electroanalytically.

According to the present invention, "partial double-stranded sections" means that the single-stranded target strands hybridize only over a portion of their total length with protective strands A), thereby forming double-stranded sections, i.e. the length of the protective strands A) is chosen so to have available single-stranded sections of the target sequence still sufficiently long for the subsequent reaction with the redox markers. These remaining single-stranded sections of the target sequence must comprise at least one thymine base. The more thymine bases are present within the single-stranded section, the more of these can be labelled with the redox marker in the subsequent step, and the higher will be the electroanalytical signals at the end and thus the sensitivity of the overall process.

Hybridization is carried out using protective strands A) which are shorter than the target strands. In this context, the length of the protective strands A) must be sufficient to enable sufficiently tight double strands to be formed. On the other hand, step c) comprises a hybridization with probe strands which are immobilized on the surface of an electrode. Since this hybridization is carried out with the protective strands A being displaced, the following must be taken into account: the probe strands should be of equal length to the protective strands or only slightly longer than the latter. It is advantageous for mismatches to be present in the target-protective strand duplex. This advantage is particularly effective if the probe strands are somewhat shorter than the protective strands. The mismatches must not occur at those sites of the target strand which harbour thymine bases, because otherwise the latter could be labelled, thus possibly influencing a later hybridization with the probe strands.

This ensures that the target strand-protective strand duplex is not more stable than the target strand-probe strand duplex, and that the protective strands are replaced with the probe strands.

According to a particular embodiment, step c) of the above method, i.e. displacement of the protective strands by the probe strands, is carried out at a temperature that is optimal for thermally stringent hybridization of probe strands and target strands. This firstly accelerates strand replacement on the electrode surface and secondly makes it more difficult for strands which are not 100% complementary to attach to the probe strands. The optimal temperature is below the "melting temperature" at which 50% of the two complementary strands are in the double-stranded form. The optimal temperature of each probe strand is determined by means of a melting curve analysis. This involves plotting an analytical signal which depends on the hybridization state against the temperature. For this purpose, UV absorption or fluorescence of the DNA is usually measured in a homogeneous solution.

Within the scope of the method according to the invention, electoanalytical detection of the target strands attached to the immobilized probe strands is preferably carried out by means of chronopotentiometry, coulometry, amperometry or voltammetry, preferably by means of square wave voltammetry (SWV), alternating current voltammetry (ACV) or cyclic voltammetry (CV). The electrodes used are metal electrodes, carbon electrodes, polymer electrodes or semiconductor electrodes, preferably wire or layer electrodes, made of gold, copper, bismuth, mercury, silver, lead, tin or alloys thereof. Preference is given to using electrodes which can be heated directly by means of an electric current or indirectly by means of a resistance heater.

The probe strands are immobilized on the surface of the electrodes by methods known to the skilled worker.

Preference is given here according to the invention to chemisorbing the probe strands onto metal electrodes, preferably by means of thiol groups (cf. for example Steel, B. A.; Herne, T. M.; Tarlov, M. J., *Anal. Chem.* 1998, 70, 4670-4677).

In a particular embodiment of the method of the invention, the double-stranded sections composed of the protective strands A and the target strands have one or more mismatches to facilitate displacement by the better fitting probe strands, i.e. having fewer mismatches.

Advantageously, the redox marker used in the method is an osmium(VIII) complex, in particular from the group consisting of [$OsO_4$(bipy)] and [$OsO_4$(py)$_2$]. A particularly preferred osmium(VIII) complex is [$OsO_4$(bipy)].

Alternatively, as described above, the redox marker may also be a molecule which consists of a 1,3-diene component and an electrochemically active component, and which reacts with the double bond of the pyrimidine rings via a Diels-Alder reaction. The reversible redox reaction may be utilized in the subsequent electroanalytical reaction for detecting the hybridization event.

In one embodiment of the invention, the electrochemically active component is selected from the group consisting of quinones, diaminobenzenes, naphtha quinones, diaminonaphthalenes, anthraquinones, phenothiazones, dihydroxybenzenes, phenylenediamines, tetrathiazanes, tetrathiafulvalenes and in each case the corresponding redox partners.

According to one embodiment of the invention, the method is carried out by removing excess redox marker molecules by dialysis from the analytical solution prior to step c), i.e. after the labelling reaction between partially protected target strands and redox markers.

According to another embodiment, the probe strands in step c) are in the hybridized form, i.e. they are hybridized with one or more nucleic acid strands (protective strands B). In this case, the labelled nucleic acid strands are hybridized in step c) on the surface of an electrode with the probe strands immobilized there, with the protective strands A and protective strands B being displaced.

Figure 2:
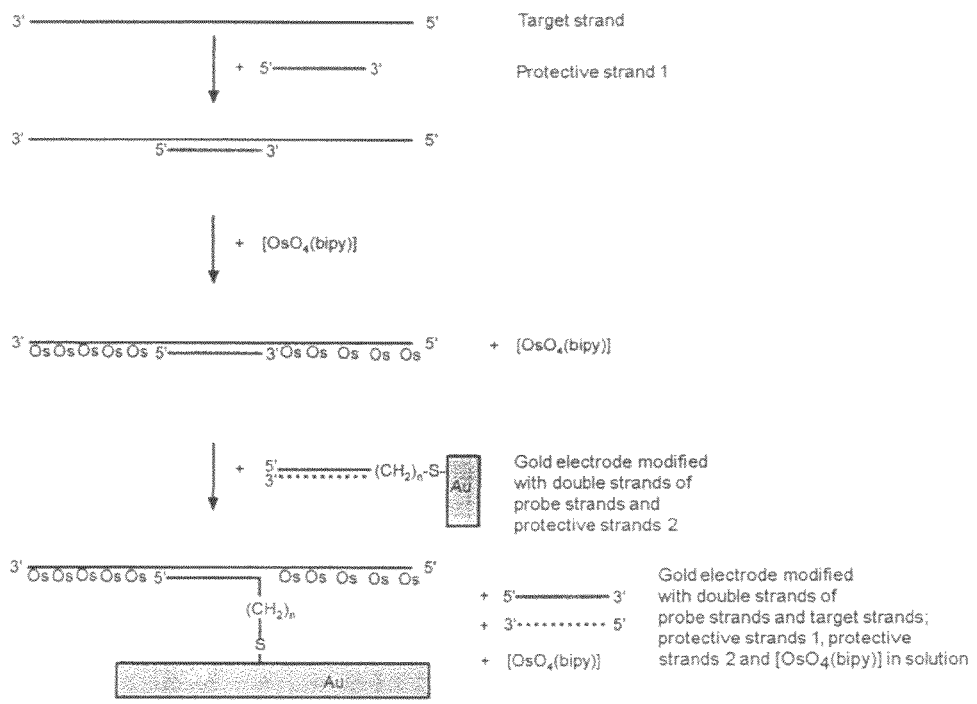
FIG. 2 schematically depicts the method according to the invention by way of a specific example.

The above-described variation of the method according to the invention is depicted schematically by way of a specific example in FIG. 2.

According to another variation of the method, the excess redox markers remain in the analytical solution after step b), and the electrochemical signals of the redox markers bound on the surface of the electrode are separated from the signals of the redox marker present in solution during detection by suitable electrochemical analytical methods. The preferred electrochemical analytical method in this variation of the method is chronocoulometry. Chronocoulometry allows electrochemical diffusion fluxes deriving from the reaction of dissolved substances to be distinguished from electrochemical fluxes caused by substances attached to the surface. In this way it is possible, for example, to determine the amount of immobilized DNA on gold electrodes by adding ruthenium hexamine chloride to the solution. The former binds to the phosphate groups of the DNA strands (cf. for example Steel, B. A.; Herne, T. M.; Tarlov, M. J., *Anal. Chem.* 1998, 70, 4670-4677).

Advantageously, the method according to the invention can be easily carried out and enables any nucleic acid strands to be labelled rapidly and easily, which then can be directly detected electrochemically.

The advantage of labelling of nucleic acids with the aid of osmium tetroxide complexes is that it can be easily carried out. The DNA-containing solution need only be admixed with the complex, for example [OsO4(bipy)], which compound then reacts spontaneously with all thymine bases in the solution that are not located in DNA double strands, i.e. that are located in DNA single strands or in single-stranded DNA sections. Other pyrimidine bases are also attacked in this way. However, cytosine reacts about 10 times more slowly than thymine. The pyrimidine base uracil replaces thymine in RNA. It differs from thymine only in the absence of a methyl group.

The second advantage is the high sensitivity achieved when the target strand comprises a plurality of thymine or uracil bases. This is because the largest proportion thereof is always present in the single-stranded section and is thus attacked by [OsO4(bipy)]. On average, each strand of a PCR product may have from 50 to 200 thymine bases. mRNA may comprise more than 500 uracil bases. This produces a signal which is enhanced more than 100 fold compared to conventional covalently bound redox markers such as, for example, ferrocene, since more than 100 electrons are reacted per target strand. Such a highly sensitive, selective and direct determination of mRNA can dispense with a normally preceding PCR step, thus enabling gene expression of cells to be analysed rapidly and easily.

The measure of the method according to the invention of hybridizing one or more sections of the target strands with a matching protective strand is advantageous in that the double-stranded section(s) thus formed is (are) insensitive to [$OsO_4$(bipy)]. In the hybridization step with the immobilized probe, the protective strand on the target strand is replaced with the probe strand. As a result, a target strand is obtained which is bound on the electrode surface and which has a very large amount of osmium-labelled pyrimidine bases. Organic molecules may mimic the behaviour of [OsO4(bipy)].

For this purpose, they comprise a 1,3-diene component in order to react with the double bond of the pyrimidine bases in accordance with a Diels-Alder reaction, forming a new ring. These molecules moreover comprise a component capable of reacting in an electrochemically reversible manner. This includes quinones, naphthaquinones, 1,4-diaminonaphthalenes, diaminobenzenes, anthraquinones, phenothiazones, tetrathiafulvalene. Both components are connected in a way such that their function is not impaired by mesomeric effects. Sterically, these molecules have been designed so as to be similar to the osmium complexes and to react, in a manner similar to the osmium compounds [$OsO_4$(bipy)] and [$OsO_4$(py)$_2$], only with the nucleic acid single strand but not with the nucleic acid double strand, and single-stranded sections thus labelled no longer form double strands with a complementary strand.

Another great advantage is the fact that all unprotected single-stranded nucleic acids are attacked by [$OsO_4$(bipy)] and thereafter no longer form any double strands. This makes it more difficult for non-complementary nucleic acid strands to attach unspecifically to the probe strands. Recognition of the target strands in an excess of non-complementary nucleic acid strands is therefore facilitated.

Together, these advantages may, in the case of mRNA to be detected, render redundant the necessity of amplification by means of PCR, since the detection sensitivity of the method according to the invention is sufficient even for very small amounts of RNA.

On average, each strand of a PCR product may have from 50 to 200 thymine bases. mRNA may comprise more than 500 uracil bases. This produces a signal which is enhanced more than 100 fold compared to conventional covalently bound redox markers such as, for example, ferrocene, since more than 100 electrons are reacted per target strand.

Such a highly sensitive, selective and direct determination of mRNA can dispense with a normally preceding PCR step, thus enabling gene expression of cells to be analysed rapidly and easily.

In addition, the method according to the invention has a substantial economic benefit, since DNA and RNA analyses are considerably simplified. Use is made of electrochemical DNA chips which, in the course of the electroanalytical methods (chronopotentiometry, amperometry, coulometry, voltammetry), provide directly readable digital analytical data, and expensive, specially labelled oligonucleotides are no longer required. In the case of gene expression analyses, expensive and time-consuming PCR amplification could be dispensed with in a best-case scenario.

More specifically, three economically interesting applications of the principle according to the invention become available:

Cost-effective preparation of labelled nucleic acid strands for use as electrochemically active reporter probes which comprise sections complementary to sections on the target strands and which recognize the latter on a molecular level, and downstream thereof an oligothymine sequence which reacts with osmium(VIII) complexes (preferably [$OsO_4$(bipy)] or the above-mentioned organic surrogates.

Rapid, simple, cost-effective electrochemical analysis of mRNA strands from gene expression without previous PCR;

Rapid, simple, cost-effective electrochemical detection of PCR products.

The present invention therefore also relates to methods for gene expression analysis and for detecting PCR products, i.e. to using the above-mentioned methods for gene expression analysis and for detecting PCR products.

The invention further relates to kits for carrying out a method for gene expression analysis and for detecting PCR products, comprising one or more nucleic acids (protective strands A), redox markers and electrodes with probes immobilized on their surface, the nucleic acid sequences of the protective strands and probes being complementary to the target strands to be detected and being shorter than the latter, and wherein it is also possible for the nucleic acid sequences of the protective strands to have one or more mismatches.

The invention further relates to electrodes for use in a method mentioned herein, on whose surface probe strands are immobilized, with the nucleic acid sequences of the probe strands being complementary to the target strands to be detected and being shorter than the latter.

The invention will also be illustrated below on the basis of examples, but is not at all limited to these specific exemplary embodiments.

EXAMPLES

Example 1

Labelling of a PCR Product with [$OsO_4$(bipy)] and Electrochemical Analysis

The procedure of determining PCR products corresponded to Example 2, said PCR products comprising the desired target sequence.

The PCR in the reaction mixture was stopped by means of protease prior to labelling. All double strands were then denatured by heating once more to 95° C. This was followed by adding a large excess (compared to the PCR products) of the protective strand. The protective strand was then attached to the PCR products under thermally stringent conditions, the reaction mixture was cooled to 35° C. and admixed with 1 mM [$OsO_4$(bipy)].

After the reaction had finished, it was possible to remove excess [$OsO_4$(bipy)] by dialysis. Finally, hybridization with gold-immobilized probe strands was carried out, with the protective strands being displaced, followed by electrochemical detection by means of square-wave voltammetry.

Example 2

Labelling of a Target Strand with [$OsO_4$(bipy)] and Electrochemical Analysis

Equimolar amounts of osmium tetroxide (available as a 2% strength solution in water, for example from Fluka) and 2,2'-bipyridyl were combined to give a 10 mM solution of the complex [$OsO_4$(bipy)]. This solution can be stored at −18° C.

After 16.5 µl (500 pmol) each of the protective strand with the sequence 5'-CGC GGA TAA CAC AGC CAC GC-3' (all oligos from Operon, Cologne, Germany) and of the target strand with the sequence 5'-TTT TTA GGT GAC TGT GTT ATC CGC A-3' had been combined at room temperature for two hours, 15 µl of the complex and 12 µl of 10 mM tris-(hydroxymethyl)-aminomethane (Tris) +0.5 M $Na_2SO_4$, pH 7.5 were added. The whole mixture was briefly agitated and then left to react at room temperature for 22 hours.

The reaction was stopped and remaining [$OsO_4$(bipy)] was removed by carrying out a dialysis in about 50 ml of 10 mM Tris buffer +0.5 M $Na_2SO_4$, pH 7.5 at 10° C. for 19 hours, using Slide-A-Lyzer MINI dialysis units from Rockford (Ill., USA) with an MWCO (molecular weight cut-off) of 3500 kDa.

To prepare the probe, the electrodes were first pretreated. The gold disc electrode was polished with aluminium oxide powder. The gold wire electrode was heated in air by a 0.65 A alternating current until red-hot. Electrochemical pretreatment was then carried out on both electrodes, comprising 25 runs of a cyclic voltammogram between −0.2 and +1.85 V versus an Ag/AgCl (3 M KCl) reference electrode in 0.5 M sulphuric acid. The electrodes were then rinsed first with water and then with ethanol. After drying, a drop (16.5 µl) of the probe strand solution (comprising 500 pmol of probe strand) was applied to the gold surface or to the plastic bridge of the wire electrode. The probe strand has the sequence 5'-TGC GGA TAA CAC AGT CAC CT-3' and is linked at the 3' end to a $CH_3$—$(CH_2)_2$—S—S—$(CH_2)_3$ disulphide linker responsible for attachment to the gold surface. The electrode was then left in a saturated water vapour atmosphere at 5° C. overnight. Next, it was rinsed off first with 0.25 M phosphate buffer, pH 7.0, then with water, and placed in a 1 mM aqueous solution of 6-mercapto-1-hexanol (MCH) for after-treatment for one hour (T. M. Herne, M. J. Tarlov, *J. Am. Chem. Soc.* 1997, 119, 8916-8920). Finally, it was rinsed off with ethanol and water.

To hybridize probe strand and target strand, the solution comprising the double strand of labelled target strand and protective strand was firstly diluted to a concentration of about 160 nM with 10 mM Tris buffer +0.5 M $Na_2SO_4$, pH 7.5 in a 10 ml glass beaker. This solution was then heated in a water bath to 80° C. for 1 minute in order to resolve the double strand and to facilitate subsequent hybridization with the probe strand.

The solution was then cooled down to a temperature of 35° C., which was set using a water bath. Work with the wire electrode was carried out in a cold solution at 3° C. (here, the temperature was then set via the heating of the wire).

Finally, hybridization was induced by immersing the electrode with the immobilized probe strand into the target strand solution. After a specific time, preferably 15 minutes, the electrode was then transferred together with the double strand into the measurement cell.

The measurements were carried out at room temperature in a measurement cell containing 20 ml of 10 mM Tris buffer +0.5 M $Na_2SO_4$, pH 7.5.

The double strand was dehybridized in 50° C. water for 30 seconds before each further measurement.

An AUTOLAB® from Eco Chemie (Utrecht, NL), equipped with a type PSTAT 10 potentiostat, was utilized for the voltammetric measurements (square wave voltammetry). The measurements were controlled using the GPES 3 software. The impulse amplitude was 40 mV and the frequency was 200 Hz with a potential step of 2 mV.

A 3-electrode arrangement with an Ag/AgCl electrode (3 M KCl) as reference electrode and a glass carbon electrode as counter electrode was used.

A gold disc electrode (diameter: 3 mm) and a heatable gold wire electrode (wire length: 4 mm, with a diameter of 25 µm) were employed as working electrode. The glass carbon, gold disc and Ag/AgCl electrodes were from Metrohm. The gold wire electrode was home-made (G.-U. Flechsig, J. Peter, G. Hartwich, J. Wang, P. Gründler, *Langmuir* 2005, 21, 7848-7853).

Heating of the wire electrode required a 100 kHz alternating current. The latter was generated by means of an FPS 15A DC power source by VOLTCRAFT®, a VOLTCRAFT® MXG-9802 function generator and a CA2100 amplifier (Concord Car Audio, Woodbury, N.Y., USA). At the end of the arrangement was a high frequency transformer. The heating currents were read with the aid of a VOLTCRAFT® M-4660A multimeter.

The relationship between the temperature of the gold wire electrode and the heating current was determined in another experiment. This involved placing the wire electrode and a counter electrode, in this case one made of glass carbon, in a measurement cell containing 50 mM potassium hexacyanoferrate (II) and 50 mM potassium hexacyanoferrate (III) in 0.1 M potassium chloride. The temperature of this solution was 3° C. The wire electrode was then heated and the difference in potential between the two electrodes was measured (potentiometrically). Using the known temperature coefficient ($\beta$=1.6 mV/K), it was possible to derive a calibration curve which reveals the temperature generated by a particular current (T. Zerihun, P. Gründler, *J. Electroanal. Chem.* 1996, 415, 85-88; T. Zerihun, P. Gründler, *J. Electroanal. Chem.* 1996, 404, 243-248).

The signal amplitude of the peak current depends on the duration and temperature of the hybridization and the concentration of the target strand. The number of labelled pyrimidine bases, thymine and cytosine, is also crucially important. In this case, 5 thymine bases were labelled.

Figure 3:
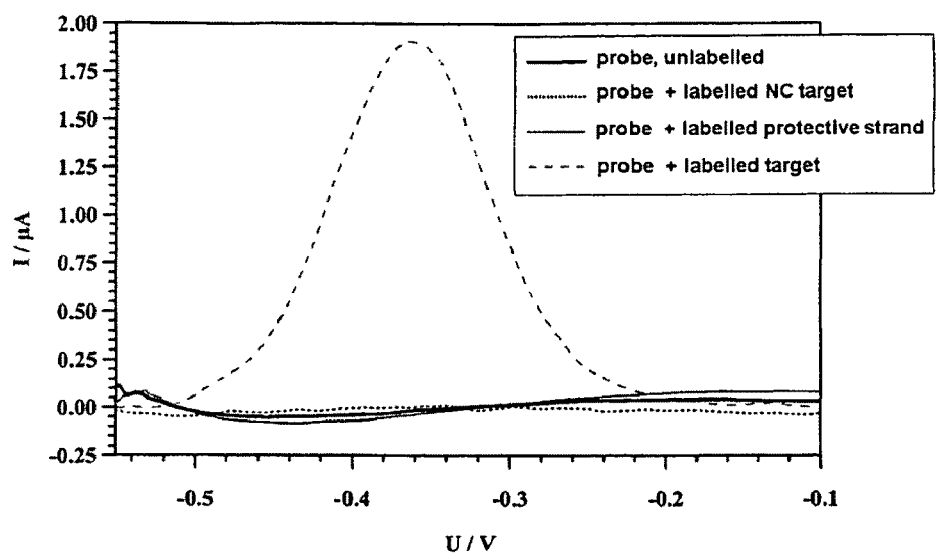
FIG. 3 depicts the voltammograms of probe strand, probe strand and labelled non-complementary target strand (NC target) ($t_H$=15 min, T=23° C., $C_{NCtarget}$=163.4 nM), probe strand and labelled protective strand ($t_H$=20 min, T=40° C., $C_{target}$=163.4 nM) and probe strand and labelled target strand ($t_H$=15 min, T=23° C., $C_{target}$=163.4 nM). Measurements in 10 mM Tris buffer+0.5 M $Na_2SO_4$ (pH=7.5). Measurements using the gold disc electrode (diameter: 3 mm) The solution was stirred during hybridization.

FIG. 3 depicts the voltammograms of probe strand, probe strand and labelled non-complementary target strand (NC target) ($t_H$=15 min, T=23° C., $C_{NC\ target}$=163.4 nM), probe strand and labelled protective strand ($t_H$=20 min, T=40° C., $C_{target}$=163.4 nM) and probe strand and labelled target strand ($t_H$=15 min, T=23° C., $C_{target}$=163.4 nM). Measurements in 10 mM Tris buffer +0.5 M $Na_2SO_4$ (pH=7.5). Measurements using the gold disc electrode (diameter: 3 mm). The solution was stirred during hybridization.

Figure 4:
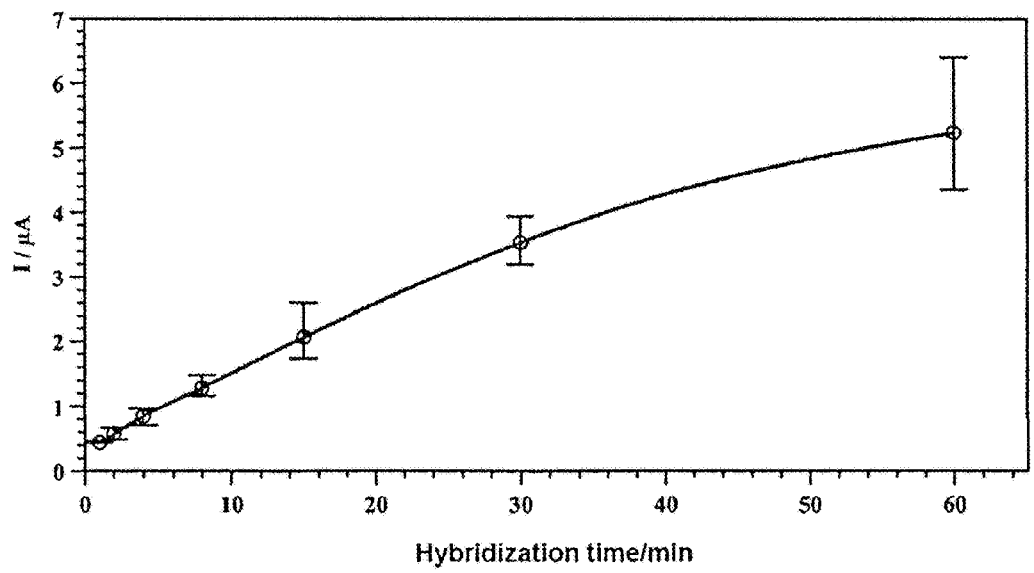
FIG. 4 depicts the signal amplitude as a function of hybridization time at 23° C. Measurements in 10 mM Tris buffer+0.5 M $Na_2SO_4$ (pH=7.5). Target strand concentration c=163.4 nM. Measurements using the gold disc electrode (diameter: 3 mm) The solution was stirred during hybridization. The averages of three measurements and the maximum deviations from the average are plotted.

FIG. 4 depicts the peak amplitude as a function of hybridization time at 23° C. Measurements in 10 mM Tris buffer +0.5 M $Na_2SO_4$ (pH=7.5). Target strand concentration c=163.4 nM. Measurements using the gold disc electrode (diameter: 3 mm). The solution was stirred during hybridization. The averages of three measurements and the maximum deviations from the average are plotted.

Figure 5:
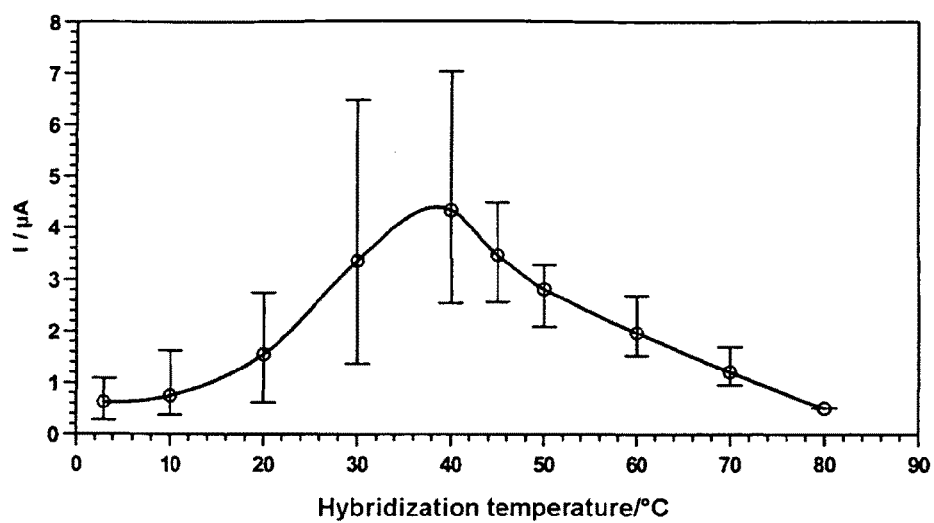
FIG. 5 describes the peak amplitude as a function of temperature. Measurements in 10 mM Tris buffer+0.5 M $Na_2SO_4$ (pH=7.5). Target strand concentration: 163.4 nM, hybridization time: 15 min. Measurements using the gold disc electrode (diameter: 3 mm) The solution was stirred during hybridization. The averages of three measurements and the maximum deviations from the average are plotted.

FIG. 5 describes the peak amplitude as a function of temperature. Measurements in 10 mM Tris buffer +0.5 M $Na_2SO_4$ (pH=7.5). Target strand concentration: 163.4 nM, hybridization time: 15 min. Measurements using the gold disc electrode (diameter: 3 mm). The solution was stirred during hybridization. The averages of three measurements and the maximum deviations from the average are plotted.

Figure 6:
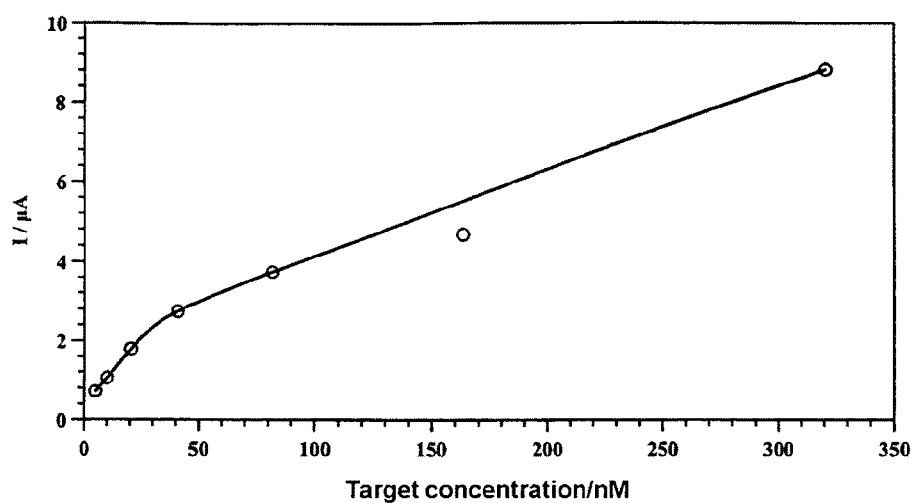
FIG. 6 depicts the peak amplitude as a function of target strand concentration. Measurements in 10 mM Tris buffer+0.5 M $Na_2SO_4$ (pH=7.5). Temperature T=40° C., hybridization time $t_H$=15 min. Measurements using the gold disc electrode (diameter: 3 mm) The solution was stirred during hybridization.

FIG. 6 depicts the peak amplitude as a function of target strand concentration. Measurements in 10 mM Tris buffer +0.5 M $Na_2SO_4$ (pH=7.5). Temperature T=40° C., hybridization time $t_H$=15 min. Measurements using the gold disc electrode (diameter: 3 mm). The solution was stirred during hybridization.

```
Target strand:      5'-TTT TTA GGT GAC TGT GTT
                    ATC CGC A-3'

Protective strand:  5'-CGC GGA TAA CAC AGC CAC
                    GC-3'

Probe strand:       5'-TGC GGA TAA CAC AGT CAC
                    CT-3'
                    with a CH3-(CH2)2-S-S-(CH2)3
                    di-sulphide linker at the
                    3' end
```

Example 3

Preparation and Use of Reporter Strands Labelled with [OsO4(bipy)]

The procedure corresponded to Example 2, but the reporter strand rather than the target strand was labelled, and the target sequence was detected by hybridizing the target strands with the labelled reporter strands and the immobilized probe strands.

In addition to the complementary sequence, the reporter strands comprised a multiplicity of thymine bases on either or both ends. The reporter strands were hybriddized with the protective strand, subsequently treated with 1 mM [$OsO_4$ (bipy)], and the solution was then purified from excess [$OsO_4$ (bipy)] by dialysis. The solution obtained in this way was added to the target solution, and the target strands were then hybridized with the probe strands immobilized on the gold electrode.

Finally, electrochemical analysis was conducted by way of square wave voltammetry. In this way it was possible to obtain multilabelled reporter strands which produce very high reversible electrochemical signals in a very inexpensive manner.

Labelling of a Reporter Strand with [OsO4(bipy)] and Electrochemical Analysis

Equimolar amounts of osmium tetroxide (available as a 2% strength solution in water, for example from Fluka) and 2,2'-bipyridyl were combined to give a 10 mM solution of the complex [$OsO_4$(bipy)]. This solution can be stored at −18° C.

After 16.5 μl (500 pmol) each of the protective strand with the sequence 5'-CGG AGG TAC GGT AAC CGG-3' (all oligos from Operon, Cologne, Germany) and of the reporter strand with the sequence 5'-TTT TTG CAG TTA CCG TAC CTC GA-3' had been combined at room temperature for two hours, 15 μl of the complex and 12 μl of 10 mM tris(hydroxymethyl)-aminomethane (Tris) +0.5 M $Na_2SO_4$, pH 7.5 were added. The whole mixture was briefly agitated and then left to react at room temperature for 22 hours.

The reaction was stopped and remaining [$OsO_4$(bipy)] was removed by carrying out a dialysis in about 50 ml of 10 mM Tris buffer +0.5 M $Na_2SO_4$, pH 7.5 at 10° C. for 19 hours, using Slide-A-Lyzer MINI dialysis units from Rockford (Ill., USA) with an MWCO (molecular weight cut-off) of 3500 kDa.

To prepare the probe, the electrodes were first pretreated. The gold disc electrode was polished with aluminium oxide powder. The gold wire electrode was heated in air by a 0.65 A alternating current until red-hot. Electrochemical pretreatment was then carried out on both electrodes, comprising 25 runs of a cyclic voltammogram between −0.2 and +1.85 V versus an Ag/AgCl (3 M KCl) reference electrode in 0.5 M sulphuric acid.

The electrodes were then rinsed first with water and then with ethanol. After drying, a drop (16.5 μl) of the probe strand solution (comprising 500 pmol of probe strand) was applied to the gold surface or to the plastic bridge of the wire electrode. The probe strand had the sequence 5'-TGC GGA TAA CAC AGT CAC CT-3' and was linked at the 3' end to a $CH_3$—$(CH_2)_2$—S—S—$(CH_2)_3$ di-sulphide linker responsible for attachment to the gold surface. The electrode was then left in a saturated water vapour atmosphere at 5° C. overnight. Next, it was rinsed off first with 0.25 M phosphate buffer (pH 7.0), then with water, and placed in a 1 mM aqueous solution of 6-mercapto-1-hexanol (MCH) for after-treatment for one hour (T. M. Herne, M. J. Tarlov, *J. Am. Chem. Soc.* 1997, 119, 8916-8920). Finally, it was rinsed off with ethanol and water.

To hybridize reporter strand and target strand (sequence: 5'-AGG TGA CTG TGT TAT CCG CAC CCC CCT CGA GGT ACG GTA ACT GC-3'), the solution containing the double strand of labelled reporter strand and protective strand was firstly introduced into a 10 ml glass beaker containing the solution of a desired concentration (e.g. 163.4 nM) of the target strand in 10 mM Tris buffer +0.5 M $Na_2SO_4$, pH 7.5. This solution was then heated in a water bath to 80° C. for 1 minute in order to resolve the double strand and to facilitate subsequent hybridization with the target strand.

After setting a desired temperature (depending on the melting point of the double strand) of the water bath, the electrode including the immobilized probe strand (for measurements using the heated wire, 3° C.; the temperature here was then set via the heating of the wire) was immersed into the solution containing the target strand labelled via the reporter strand. After minutes, the electrode together with the double strand was then transferred to the measurement cell.

The measurements were carried out at room temperature in a measurement cell containing 20 ml of 10 mM Tris buffer +0.5 M $Na_2SO_4$, pH 7.5.

The double strand was dehybridized in 50° C. water for 30 seconds before each further measurement.

An AUTOLAB® from Eco Chemie (Utrecht, NL), equipped with a type PSTAT 10 potentiostat, was utilized for the voltammetric measurements (square wave voltammetry). The measurements were controlled using the GPES 3 software. The impulse amplitude was 40 mV and the frequency was 200 Hz with a potential step of 2 mV.

A 3-electrode arrangement with an Ag/AgCl electrode (3 M KCl) as reference electrode and a glass carbon electrode as counter electrode was used.

A gold disc electrode (diameter: 3 mm) and a heatable gold wire electrode (wire length: 4 mm, with a diameter of 25 μm) were employed as working electrode. The glass carbon, gold disc and Ag/AgCl electrodes were from Metrohm. The gold wire electrode was home-made (G.-U. Flechsig, J. Peter, G. Hartwich, J. Wang, P. Gründler, *Langmuir* 2005, 21, 7848-7853).

Heating of the wire electrode required a 100 kHz alternating current. The latter was generated by means of an FPS 15A DC power source by VOLTCRAFT®, a VOLTCRAFT® MXG-9802 function generator and a CA2100 amplifier (Concord Car Audio, Woodbury, N.Y., USA). At the end of the arrangement was a high frequency transformer. The heating currents were read with the aid of a VOLTCRAFT® M-4660A multimeter.

The relationship between the temperature of the gold wire electrode and the heating current was determined in another experiment. This involved placing the wire electrode and a counter electrode, in this case one made of glass carbon, in a measurement cell containing 50 mM potassium hexacyanoferrate (II) and 50 mM potassium hexacyanoferrate (III) in 0.1 M potassium chloride. The temperature of this solution was 3° C. The wire electrode was then heated and the difference in potential between the two electrodes was measured (potentiometrically). Using the known temperature coefficient ($\beta$=1.6 mV/K), it was possible to derive a calibration curve which revealed the temperature gene-rated by a particular current (T. Zerihun, P. Gründler, *J. Electroanal. Chem.* 1996, 415, 85-88; T. Zerihun, P. Gründler, *J. Electroanal. Chem.* 1996, 404, 243-248).

| | |
|---|---|
| Reporter strand: | 5'-TTT TTG CAG TTA CCG TAC CTC GA-3' |
| Target strand: | 5'-AGG TGA CTG TGT TAT CCG CAC CCC CCT CGA GGT ACG GTA ACT GC-3' |
| Protective strand: | 5'-CGG AGG TAC GGT AAC CGG-3' |
| Probe strand: | 5'-TGC GGA TAA CAC AGT CAC CT-3' with a $CH_3$—$(CH_2)_2$—S—S—$(CH_2)_3$ di-sulphide linker at the 3' end |

Example 4

Studying Gene Expression by Labelling the mRNA Copies with [OsO4(bipy)]

The method was carried out in a manner similar to Example 2, with mRNA representing the target strands.

The nucleic acid extracts of a cell sample or tissue sample were hybridized with the protective strands corresponding to a sequence section of the desired expressed gene. Then 1 mN [$OsO_4$(bipy)] was added. Most of the nucleic acid strands were modified with osmium in the process and were no longer capable of forming double strands. Only the protected sections of the mRNA copies were then able to hybridize with the gold-immobilized probe strands, with the protective strands being displaced. This firstly produced a high selectivity and secondly a very high sensitivity in the sub-sequent electrochemical analysis by means of chronopotentiometry. It was therefore possible to dispense with amplification of the mRNA copies by RT PCR and PCR.

Example 5

Electrochemical Analysis of Osmium-Labelled Nucleic Acids Immediately after the Labelling Reaction without Prior Removal of Excess Dissolved [OsO$_4$(bipy)]

The method is carried out in a manner similar to Example 2, but no dialysis is performed after the labelling reaction, and as a result excess labelling reagent remains in the sample solution. This solution is then contacted with the working electrode modified with the probe strand for hybridization.

By applying chronocoulometry (A. B. Steel, T. M. Herne, M. J. Tarlov, *Anal. Chem.* 1998, 70, 4670-4677) it was possible to distinguish between the electrochemical signals of the immobilized osmium compounds and those of the dissolved [OsO$_4$(bipy)] molecules.

For this purpose, a potential step experiment is carried out. The potential is changed from −0.2 to −0.4 V. The time of this change is set to zero, and the charge measured is subsequently plotted as a function of sqrt(t). The chronocoulometric intersections of the extended linear sections with the y axis (at t=0) indicate the charges caused by capacitive currents and faradayic currents of immobilized substances, here due to conversion of the immobilized and labelled nucleic acids.

Example 6

Labelling and Detection of Nucleic Acid Strands with the Aid of a Diene-Quinone Compound The pyrimidine bases were modified by a Diels-Alder reaction with the 1,3-diene component of this organic compound. This marker was detected electrochemically by way of the reversibly redox-active quinone component.

The method is conducted in a manner similar to Example 2, but 7,8-bis(methylene)-6,9-dihydronaphthoquinone rather than the osmium compound is employed for labelling the nucleic acids.

---

The invention claimed is:

1. A method of detecting nucleic acid strands comprising labelling nucleic acid strands with redox markers and detecting the labeled strands via electrochemical detection of hybridization events, wherein
   a) single-stranded nucleic acid strands (target strands) are hybridized with one or more nucleic acid strands (protective strands A), wherein the protective strands A are shorter than the target strands in order to form partial double-stranded sections,
   b) wherein the remaining single-stranded sections of the target strands are labelled by reaction with redox markers, wherein the redox markers react selectively with double bond of the pyrimidine rings of the nucleic acid strands via Diels-Alder reaction, or wherein the redox markers are osmium (VII) complexes,
   c) wherein the labeled nucleic acid strands are hybridized on the surface of an electrode with probe strands immobilized there, with the protective strands A being displaced, and
   d) wherein the nucleic acid strands hybridized to the probe strands are then detected electroanalytically.

2. The method according to claim 1, characterized in that the protective strands A are displaced by the probe strands in step c) at a temperature that is optimal for thermally stringent hybridization of probe strands and target strands.

3. The method according to claim 1, characterized in that the electrode is a heated electrode.

4. The method according to claim 1, characterized in that the double-stranded sections of protective strands A and target strands have one or more mismatches.

5. The method according to claim 1, characterized in that the redox marker is an osmium(VIII) complex.

6. The method according to claim 5, characterized in that the osmium(VIII) complex is $OsO_4$(bipy).

7. The method according to claim 1, characterized in that the redox marker is a molecule consisting of an electrochemically active component and a 1,3-diene component which reacts with double bonds of the pyrimidine rings via a Diels-Alder reaction.

8. The method according to claim 7, characterized in that the electrochemically active component is selected from the group consisting of quinones, diaminobenzenes, naphtha quinones, diaminonaphthalenes, anthraquinones, phenothiazones, dihydroxybenzenes, phenylenediamines, tetrathiazanes, tetrathiafulvalenes and in each case the corresponding redox partners.

9. The method according to claim 1, further comprising removing the excess redox markers from the analytical solution by dialysis prior to step c).

10. The method according to claim 1, wherein the method further comprises hybridizing one or more probe strands with one or more nucleic acid strands (protective strands B) prior to hybridizing the labeled nucleic acid strand in step c) and wherein hybridizing the labeled target strands with probe strands immobilized on the surface of an electrode in step c) displaces the protective strands A and protective strands B.

11. The method according to claim 1, characterized in that the excess redox markers remain in the analytical solution after step b), and the electrochemical signals of the redox markers bound on the surface of the electrode are separated from the signals of the redox markers present in solution during detection by suitable electrochemical analytical methods.

12. The method according to claim 11, characterized in that the electrochemical analytical method is chronocoulometry.

13. The method according to claim 11, characterized in that the electrochemical analytical method is chronopotentiometry.

14. The method according to claim 1 for gene expression analysis.

15. The method according to claim 1 for detecting PCR products.

* * * * *

SEQUENCE LISTING

```
<160> NUMBER OF SEQ ID NOS: 7

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 1
tttttaggtg actgtgttat ccgca                                           25

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 2
cgcggataac acagccacgc                                                 20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 3
tgcggataac acagtcacct                                                 20

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 4
```

```
tttttgcagt taccgtacct cga                                              23

<210> SEQ ID NO 5
<211> LENGTH: 44
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 5
aggtgactgt gttatccgca cccccctcga ggtacggtaa ctgc                       44

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 6
cggaggtacg gtaaccgg                                                    18

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 7
tgcggataac acagtcacct                                                  20
```